United States Patent [19]
Lobet et al.

[11] Patent Number: 6,113,914
[45] Date of Patent: Sep. 5, 2000

[54] OSP A PROTEINS OF *BORRELIA BURGDORFERI* SUBGROUPS, ENCODING GENES AND VACCINES

[75] Inventors: Yves Lobet, Rixensart, Belgium; Markus Simon; Ulrich Schaible, both of Frieburg, Germany; Reinhard Wallich, Heidelberg, Germany; Michael Kramer, Frieburg, Germany

[73] Assignee: Smithkline Beecham Biologicals (S.A.), Rixensart, Belgium

[21] Appl. No.: 08/193,159

[22] PCT Filed: Aug. 11, 1992

[86] PCT No.: PCT/EP92/01827

§ 371 Date: Jul. 5, 1994

§ 102(e) Date: Jul. 5, 1994

[87] PCT Pub. No.: WO93/04175

PCT Pub. Date: Mar. 4, 1993

[30] Foreign Application Priority Data

Aug. 15, 1991 [GB] United Kingdom .................... 9117602
Oct. 21, 1991 [GB] United Kingdom .................... 9122301
May 28, 1992 [GB] United Kingdom .................... 9211317
May 28, 1992 [GB] United Kingdom .................... 9211318

[51] Int. Cl.$^7$ .......................... A61K 39/00; A61K 39/02; A61K 39/116; G01N 33/554
[52] U.S. Cl. ..................................... 424/234.1; 424/184.1; 424/185.1; 424/190.1; 424/203.1; 435/7.32; 435/69.3; 435/71.2; 436/543; 530/350; 530/359; 530/403; 530/806; 530/820; 530/825
[58] Field of Search ............................. 424/234.1, 184.1, 424/185.1, 190.1, 203.1; 435/7.32, 69.3, 71.2; 436/543; 530/359, 403, 806, 820, 350, 825

[56] References Cited

U.S. PATENT DOCUMENTS

| 5,178,859 | 1/1993 | Simon et al. . | |
| 5,434,077 | 7/1995 | Simon et al. . | |
| 5,523,089 | 6/1996 | Bergstrom ............................ | 424/262.1 |
| 5,688,512 | 11/1997 | Bergstrom et al. .................. | 424/234.1 |

FOREIGN PATENT DOCUMENTS

| 2025597 | 3/1991 | Canada . | |
| 0366238 | 5/1909 | European Pat. Off. ........ | C12N 15/44 |
| 0 366 238-A | 5/1990 | European Pat. Off. . | |
| 0 418 827-A | 3/1991 | European Pat. Off. . | |
| 9004411 | 5/1990 | WIPO ............................ | A61K 39/02 |
| WO 92/00055 | 1/1992 | WIPO . | |

OTHER PUBLICATIONS

P.A. Rosa, et al., "Molecular Analysis of the Major Outer Surface Protein Locus from a Divergent *Borrelia burgdorferi* Isolate from Europe", (1992), Current Communications in Cell Molecular, vol. 6, pp. 95–110.

B. Luft, et al., "Analysis and expression of the *Borrelia burgdorferi* P/Gau fla gene: Identification of hetergeneity with the B31 strain", (1992), FEMS Microbiology Letters, vol. 93/1, pp. 63–67.

H. Eiffert, et al., "Nucleotide Sequence of the ospAB Operon of a *Borrelia burgdorferi* Strain Expressing OspA but Not OspB", (1992), Infection and Immunity, vol. 60, No. 5, pp. 1864–1868.

R. Houghten, et al., "Relative Importance of Position and Individual Amino Acid Residues in Peptide Antigen–Antibody Interactions: Implications in the Mechanism of Antigenic Drift and Antigenic Shift", (1986), Vaccines 86. pp. 21–25.

P.A. Rosa, et al., "Recombination between genes encoding major outer surface proteins A and B of *Borrelia burgdorferi*", (1992), Molecular Microbiology, vol. 6(20), pp. 3031–3040.

S. Bergstrom,e t al., "Molecular analysis of linear plasmid–encoded major surface proteins, OspA and OspB, of the Lyme disease spirchaete *Borrelia burgdorferi*", (1989), Molecular Microbiology, vol. 3(4), pp. 479–486.

R. Wallich, et al., "Cloning and sequencing of the gene encoding the outer surface protein A (OspA) of a European *Borrelia burgdorferi* isolate", (1989), Nucleic Acids Research, vol. 17, No. 21, p. 8864.

U.E. Schaible, et al., "The Severe Combined Immunodeficiency (scid) Mouse", (1989), J. Exp. Med., vol. 170, pp. 1427–1432.

E. Fikrig, et al., "Protection of Mice Against the Lyme Disease Agent by Immunizing with Recombinant OspA", (1990), Science, vol. 250, pp. 553–556.

E. Fikrig, et al., "Long–Term Protection of Mice From Lyme by Vaccination with OspA", (1992), Infection and Immunity, vol. 60, No. 3, pp. 773–777.

U.E. Schaible, et al., "Immune sera to individual *Borrelia burgdorferi* isolates or recombinant OspA thereof protect SCID mice against infection with homologous strains but only partially or not at all against those of different OspA/OspB genotype", (1993), Vaccine, vol. 11, No. 10, pp. 1–49–1053.

Kramer et al. Immunobiol. 181:357–366, 1990.

Schaible et al. J. Exp. Med. 170:1427–1432, 1989.

Wallich et al. Infection and Immunity 60(11):4856–4866, 1992.

Schaible, U.E. et al., J. Exp. Med., vol. 170, pp. 1427–1432, Oct. 1989.

Schaible, U.E. et al., Proc. Natl. Acad. Sci. USA, vol. 87, pp. 3768–3772, May 1990.

(List continued on next page.)

*Primary Examiner*—James C. Housel
*Assistant Examiner*—V. Ryan
*Attorney, Agent, or Firm*—Wayne J. Dustman; William T. King; Charles M. Kinzig

[57] ABSTRACT

The invention relates to novel Borrelia, and OspA antigens derived therefrom. These antigens show little homology with known OspA's and are therefore useful as vaccine and diagnostic reagents. Multicomponent vaccines based on OspA's from different Borrelia groups are also disclosed.

15 Claims, 1 Drawing Sheet

OTHER PUBLICATIONS

Kramer, M.D. et al., Immunobiol., vol. 181, pp. 357–366, 1990.

Simon, M.M. et al., J. Infect. Dis., vol. 164, pp. 123–132, 1991.

Geneseq Protein Database, Accession No. X66065, Derwent Publications Ltd, Jun. 3, 1992, London, GB, R.Wallich et al.

Abstracts of the annual meeting of the American Society for Microbiology, abstract No. B–238, vol. 91, No. 0, 1991, Washington, US, p. 65, S. Bergström et al.

Der Hautarzt, vol. 41, No. 12, 1990, Berlin, FRG, pp. 648–657, M. D. Kramer et al., see p. 654, left col., 3rd paragraph.

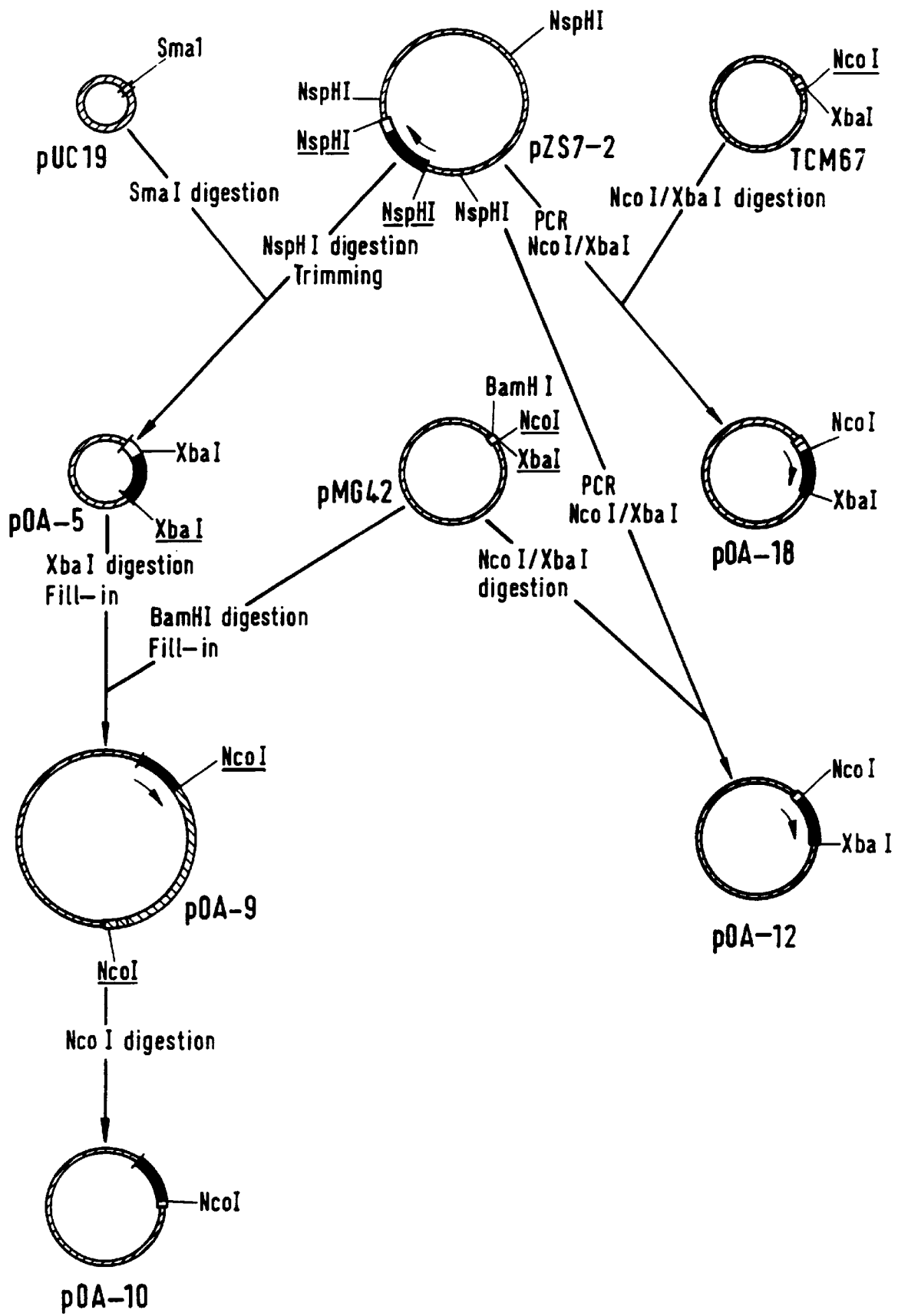

OSP A PROTEINS OF *BORRELIA BURGDORFERI* SUBGROUPS, ENCODING GENES AND VACCINES

The present invention relates to novel antigens, to methods for their production, to compositions containing them and to their use in the prevention, treatment and diagnosis of Lyme Disease in humans and other animals. In particular the present invention discloses novel serotypes/genotypes of the outer surface protein (Osp A) from the spirochete *Borrelia burgdorferi*, the causative agent of Lyme disease, and vaccine and diagnostic reagents based on *B. burgdorferi* of more than one subgroup.

Lyme disease in humans is a chronic progressive disease caused by *B burgdorferi*, which is transmitted to humans mainly by Ixodes ticks. The disease attacks many organs, notably the skin, heart, liver, central and peripheral nervous system, kidneys as well as the musculoskeletal system.

Lyme disease itself is the most common vector borne infection in the USA and has been reported in every continent except Antarctica.

A number of groups have isolated and proposed the major surface protein (Osp A) of *B. burgdorferi*, as being a potential vaccine candidate for use against Lyme disease. For example, International patent application published under WO90/04411 (SIMBICOM) discloses the cloning and expression of an Osp A protein derived from *B. burgdorferi* B31 and its use as a vaccine, M. M. Simon and colleagues have cloned and expressed Osp A from *B. burgdorferi* ZS7 (European Patent Application No. 90117943.2 published under No. 0418 827), and demonstrated its protective capacity to induce antibodies in passively immunised SCID mice (PNAS: 87 1990, 3768–3772). Flavell and colleagues (Science (1991) 250 p553–556) have cloned and expressed the gene for Osp A from *B. burgdorferi*, N40 and have demonstrated its protective efficacy in C3H/He mice.

All isolates of *B. burgdorferi* identified above appear to be closely related. However we have now identified six subgroups of *B. burgdorferi* by analysing 55 spirochete isolates from different geographical areas and sources with a series of immunological, biochemical and molecular genetic techniques. The finding of different subgroups of *B. burgdorferi* isolates have important implications for both effective vaccination and diagnosis of Lyme disease. Since ELISA diagnostic assays directed against a strain of which species N40 is a member would not or only partially cross react with species from other subgroups. Equally a vaccine based on only one Osp A for example from N40 would not provide optimal protection against *B. burgdorferi* from a different subgroup.

The present inventors have identified five additional subgroups of *B. burgdorferi* based on their Southern blotting and PCR amplification of Osp A sequences, and differences in the amino acid and nucleic acid sequences themselves and also in reactivity against monoclonal antibodies to Osp A proteins.

The surprising discovery that *B. burgdorferi* exhibits such heterogeneity has important implications for vaccines against, and diagnostics reagents for the detection of, Lyme disease, since vaccines or diagnostic based on an Osp A from one group of *B. burgdorferi* may not detect or protect against infection of *B. burgdorferi* from a second group. Indeed the present inventors have shown that whereas protection can be afforded by anti Osp A antibodies generated by recombinant Osp A or viable or killed organisms within a group of closely related strains, no or only partial, protection is observed if challenge is made with an organism from a different group.

A first subtype having representative ZS7, B31, N40 is referred to herein as group I (alternative nomenclature refers to group I strains as group A).

A second subgroup hereinafter group II (alternatively known as group B) is herein disclosed and is exemplified by the species ZQ1. This species has been deposited at the DSM Deutsche Sammlung von Mikroorganismen Und Zellkulturen of Mascheroderweg 91B D-3300 Braunschweig on Jul. 11, 1991 and given the accession No. DSM6606. This group is distinct in a number of ways from group I.

Firstly, plasmid analysis of strain ZQ1 when compared with representatives from group I shows that ZQ1 has at least two unique plasmids of 18 and 14 Kd. Furthermore plasmid of 16 Kb found in group I strains is absent from strain ZQ1. Secondly when examined by polyacrylamide gel electrophoresis Osp A from ZQ1 has an apparent molecular weight of 32 Kd.

Thirdly various monoclonal antibodies specific for Osp A of group I, such as the antibodies designated LA2 L26 LA28 LA33 do not react with Osp A from group II. LA2 and LA26 antibody are known and have been described in European patent application No. EP0418827. The hybridoma producing LA2 has been deposited under accession No. ECACC 89 09 1302 on Sep. 13, 1989 at the European Collection of animal cell cultures, Public health laboratory services Porton Down Wiltshire SP40J9. The hybridoma producing LA26 has been deposited at the same culture collection under accession No. 9005406 on Jun. 28, 1990.

However an other monoclonal antibody, LA31.1, does react with the Osp A species of subgroups I and II suggesting common epitopes among Osp A species of different subgroups do exist.

We have also characterised Osp A DNA from group II strains by PCR amplification. Two pairs of Osp A primers were used, these being designated prOsp A1-prOsp A4 and prOsp A1-prOsp A2.

The primers have the following sequences:

```
prOsp A1: 5'-GGGAATAGGT CTAATATTAG CC-3' prOsp A2: 5'-TGCCTGAATT CCAAGCTGCA-3' prOsp A4: 5'-GCAGTTAAAG TTCCTTCAAG AACATAGC-3'
``` and correspond to nucleotides at positions 138–160 (prOsp A1), 611–638 (prOsp A4), and 759–778 (prOsp A2), of ZS7 Osp A respectively. Total DNA of Group II, *B. burgdorferi* are distinguishable from that of Group I in that group II will not permit successful PCR (polymerase chain reaction) amplification when prOsp A1 and prOsp A2 are used as primers whereas total DNA from group I will permit a successful reaction. In contrast, when prOsp A1 and prOsp A4 are used as primers, then both DNA's of group I and group II will undergo polymerase chain reaction.

These results show that group II, *B. burgdorferi* have a different Osp A sequences to group I Osp As.

Equally, group II Osp A DNA, can be distinguished from group I Osp A DNA by Southern blotting utilising Osp A ZS7 sequence as a probe. Digesting genomic DNA of *B. burgdorferi* group II with the restriction enzyme Hind III shows a different banding pattern than that of group I strain.

For example a group I strain reveals two hybridisation fragments of 1.2 kb and 0.3 kb whereas a group II strain expressed two fragments of 0.9 kb and 0.4 kb.

Also, passive immunisation of SCID mice with immune sera to Osp A from group II will not protect against *B. burgdorferi* group I challenge.

Finally when compared to the sequence of Osp A ZS7 the DNA and amino acid sequence of ZQ1 strain Osp A Sequence ID 1 and 2 (i.e. a group II strain), demonstrates the substantial variation between a group I and group II strain at both the DNA and amino acid levels.

The surprising inability to protect against heterologous challenge means that a vaccines based on a single Osp A from a group I organism may be ineffective against infection with *B. burgdorferi* from group II organism and vice versa. Consequently there is a need for a vaccine which will protect against group II infection.

Accordingly there is provided DNA sequence encoding an Osp A derived from a *B. burgdorferi* characterised in that polymerase chain reaction amplification will take place utilising prOsp A1–A4 primers, but not prOsp A1–A2, and the invention further provides purified or isolated Osp A encoded thereby.

Preferably the Osp A of the present invention will not react with monoclonal antibody LA2 or LA26. Most preferably the Osp A of the present invention will have a relative molecular weight of 32 kDa as determined by SDS electrophoresis utilising molecular weight markers as standard.

Preferably the Osp A is derived from either ZQ1 or NE11H or other group II strain.

Preferably the protein is at least 70% pure as determined by SDS polyacrylamide gel electrophoresis, in particular at least 80% pure, and most preferably at least 95% pure. Preferably the Osp A antigen has a relative molecular weight of 32 kDa as determined by SDS polyacrylamide gel electrophoresis. Preferably the Osp A antigen will not react with the monoclonal antibody LA2.

In another aspect of the present invention there is provided a DNA sequence substantially identical to the DNA sequence encoding Osp A from ZQ1. By substantially identical it is meant a DNA sequence contains a sequence which is at least 85% identical and preferably 90% identical to the ZQ1 Osp A sequence depicted in Sequence ID 1. The mature protein starts at position 17 and preferably the invention provides a DNA sequence which is at least 95% identical to the sequence encoding the mature protein as indicated in Sequence ID 2.

In an alternative embodiment there is provided an Osp A containing an amino acid sequence substantially identical to the sequence set forth in sequence ID 2. The term substantially identical in relation to the amino acid sequence means amino acid sequence which is at least 85% and preferably 90% identical to the protein sequence depicted in figure and preferably at least 85% identical to the mature protein.

The present inventors have also found utilising the same biochemical and immunological techniques other groups of *B. burgdorferi* unrelated to other group I or II. Two isolates characteristic of group III (or group C) are the strain designated as 19857 and 21038. Such strains, like group II, strains react under PCR conditions with prOsp A1–A2 but not with prOsp A1–A4. However they differ from group II strains when analysed by Southern blotting when utilising a ZS7 probe and restriction enzyme HindIII. Such analysis reveal hybridisation fragments of 4.0 kb and 0.5 kb. In addition they react with monoclonal antibody LA26, but not LA2.

We have now sequenced utilising PCR technology, and expressed a DNA sequence encoding an Osp A from strain 19857. The DNA and amino acid sequence are depicted in sequence ID No. 3 and 4. A comparison with sequence from other groups shows that the Osp A only has approximately 65% identity at the DNA and amino acid levels with Osp A from other subgroups.

Accordingly the present invention provides a DNA sequence encoding an Osp A protein wherein the DNA sequence is substantially identical to the DNA sequence of Sequence ID 3. In a further embodiment there is provided an Osp A protein which has an amino acid sequence substantially identical to the protein as disclosed in Sequence ID 4.

The term substantial identical as used herein with respect to the sequences depicted in sequence ID No.3 and 4 mean at least 70% identity, preferably 80–85% identity, more preferably 85–95% identical.

A fourth subgroup, group IV (or group D) of *B. burgdorferi*, as exemplified by a Swedish isolate ACA-1 differs from any of groups I, II or m, M. Jonsson et al.(Int. Conf. Lyme Borreliosis 1990). This group will not undergo PCR with either prOsp A1–A2 or prOsp A1–A4. Their Osp A's react with monoclonal antibody LA26 but not with LA2.

Southern blotting analysis when utilising a ZS7 probe and restriction enzyme HindIII reveal a single hybridisation fragment of about 1.7 kb.

Isolated or recombinant Osp A from group IV also form part of the present invention as do vaccine or diagnostic compositions containing them.

By utilising the same Biochemical techniques, the present inventors have identified representatives from group V and group VI. A group V isolates is known as 20047 and a representative of group VI is the strain known as S90.

Isolated Osp A from a group V and VI strain also form part of the invention.

The present invention also relates to immunogenic derivatives of the OspA from group II, group III, group IV and group V or group VI *B. burgdorferi*.

The term immunogenic derivative as used herein encompasses any molecule such as a truncated or hybrid protein which are immunologically reactive with antibodies generated by infection of a mammalian host with a group II, or group III or group IV, or group V or group VI, *B. burgdorferi* and which preferably do not react with the monoclonal antibodies designated LA2. Such derivatives may be prepared by substitution, or rearrangement of aminoacids or by chemical modifications thereof.

Immunogenic fragments of the protein, which may be useful in the preparation of subunit vaccines, may be prepared by expression of the appropriate gene fragments or by peptide synthesis, for example using the Merrifield synthesis (The Peptides, Vol 2., Academic Press, NY, page 3).

The immunogenic derivative of the invention can be a hybrid, that is, a fusion polypeptide containing additional sequences which can carry one or more epitopes for other *B. burgdorferi* immunogens including Osp A and/or Osp B, or other immunogens from, for example other pathogens. Alternatively, the immunogenic derivative of the invention can be fused to a carrier polypeptide such Hepatitis B surface or core antigen or to another carrier which has immunostimulating properties, as in the case of an adjuvant, or which otherwise enhances the immune response to the Osp A protein or derivative thereof, or which is useful in expressing, purifying or formulating the protein or derivative thereof.

The invention also extends to the Osp A protein or immunogenic derivative thereof when chemically conjugated to a macromolecule using a conventional linking agent such as glutaraldehyde (Geerlings et al, (1988) J. Immunol. Methods, 106, 239–244).

Particularly preferred derivatives are hybrid fusion proteins of the influenza non-structural protein NS1 and Osp A or truncated Osp A derivatives. These can advantageously be produced by recombinant DNA techniques in high yields in *E. coli*.

Accordingly the present invention provides an Osp A protein fused to the N terminal portion of the protein NS1 from Influenza. Preferably the Osp A portion of the fusion protein is truncated so as to remove at least the hydrophobic signal sequence. More preferably the N terminal 16 amino acids representing the signal sequence and the cysteine residue which is the first amino-acid of the mature protein of the Osp A are missing.

Preferably the NS1 part of the fusion protein comprises from 3 to 81 amino acids of the N-terminal portion of the gene. The longer the NS1 part of the fusion is preferred, since this permits higher expression levels of proteins.

These hybrid proteins of the present invention are recoverable from the soluble fraction as non aggregated protein, in contrast to the native recombinant Osp A and are expressed at a higher level. The proteins retain their ability to react with monoclonal antibodies raised against native Osp A and are capable of raising a protective immune response in laboratory animals eg mice and rabbits.

In an embodiment of the invention there is provided an NS1 Osp A fusion protein from the Osp A group, known as group I, eg an Osp A from strain ZS7 as disclosed in EP 0418-827, or B31 as described by Howe et al. Science 227 p645, 1985, or N40 as described by Flavell et al. Such Osp A's show significant sequence homology at both the DNA and amino acid levels and are cross protective.

In a further embodiment of the present invention there is provided an NS1-Osp A wherein the Osp A is from the group known as group II. For example the Osp from *B. burgdorferi* strain ZQ1 as described herein.

In a yet further embodiment of the present invention there is provided an NS1-Osp A wherein the Osp A is from the group known as group III. For example strain 19857. The invention further provides a group IV NS1-Osp A, for example wherein the Osp A is derived from the strain AcaI.

The present invention further provides a DNA sequence which encodes an NS1- Osp A fusion protein as described herein. In particular the present invention provides a DNA sequence encoding an NS1-Osp A protein and the protein itself as shown in Sequence ID Nos 5 to 12 attached herewith.

The proteins of the present invention can be produced by methods standard in the art for producing other Osp A proteins from known strains. For example, the Osp A proteins maybe produced in *E. coli* utilising recombinant DNA technology. In particular, the proteins may be produced as full length immature proteins or mature proteins. The proteins may also be expressed as fusion proteins, such as NS1-fusion proteins.

A DNA sequence encoding the proteins of the present invention (eg Osp A ZQ1 or Osp A 19857) can be synthesized using standard DNA synthesis techniques, such as by enzymatic ligation as described by D. M. Roberts et al in Biochemistry 1985, 24, 5090–5098, by chemical synthesis, by in vitro enzymatic polymerization, or by PCR technology utilising for example a heat stable polymerase, or by a combination of these techniques.

Enzymatic polymerisation of DNA may be carried out in vitro using a DNA polymerase such as DNA polymerase I (Klenow fragment) in an appropriate buffer containing the nucleoside triphosphates dATP, dCTP, dGTP and dTTP as required at a temperature of 10°–37° C., generally in a volume of 50 µl or less. Enzymatic ligation of DNA fragments may be carried out using a DNA ligase such as T4 DNA ligase in an appropriate buffer, such as 0.05M Tris (pH 7.4), 0.01M MgCl$_2$, 0.01M dithiothreitol, 1 mM spermidine, 1 mM ATP and 0.1 mg/ml bovine serum albumin, at a temperature of 4° C. to ambient, generally in a volume of 50 ml or less. The chemical synthesis of the DNA polymer or fragments may be carried out by conventional phosphotriester, phosphite or phosphoramidite chemistry, using solid phase techniques such as those described in 'Chemical and Enzymatic Synthesis of Gene Fragments—A Laboratory Manual' (ed. H. G. Gassen and A. Lang), Verlag Chemie, Weinheim (1982),or in other scientific publications, for example M. J. Gait, H. W. D. Matthes, M. Singh, B. S. Sproat, and R. C. Titmas, Nucleic Acids Research, 1982, 10, 6243; B. S. Sproat and W. Bannwarth, Tetrahedron Letters, 1983, 24, 5771; M. D. Matteucci and M. H. Caruthers, Tetrahedron Letters, 1980, 21, 719; M. D. Matteucci and M. H. Caruthers, Journal of the American Chemical Society, 1981, 103, 3185; S. P. Adams et al., Journal of the American Chemical Society,1983, 105, 661; N. D. Sinha, J. Biernat, J. McMannus, and H. Koester, Nucleic Acids Research, 1984, 12, 4539; and H. W. D. Matthes et al., EMBO Journal, 1984, 3, 801.

Alternatively, the coding sequence can be derived from *B. burgdorferi* mRNA, using known techniques (e.g. reverse transcription of mRNA to generate a complementary cDNA strand), and commercially available cDNA kits.

DNA polymers which encode mutants of the Osp A proteins may be prepared by site-directed mutagenesis of the cDNA which codes for the protein by conventional methods such as those described by G. Winter et al in Nature 1982, 299, 756–758 or by Zoller and Smith 1982; Nucl. Acids Res., 10, 6487–6500, or deletion mutagenesis such as described by Chan and Smith in Nucl. Acids Res., 1984, 12, 2407–2419 or by G. Winter et al in Biochem. Soc. Trans., 1984, 12, 224–225.

The process of the invention may be performed by conventional recombinant techniques such as described in Maniatis et. al., Molecular Cloning—A Laboratory Manual; Cold Spring Harbor, 1982–1989.

In particular, the process may comprise the steps of:

i) preparing a replicable or integrating expression vector capable, in a host cell, of expressing a DNA polymer comprising a nucleotide sequence that encodes the protein or an immunogenic derivative thereof;

ii) transforming a host cell with said vector;

iii) culturing said transformed host cell under conditions permitting expression of said DNA polymer to produce said protein; and iv) recovering said protein.

The term 'transforming' is used herein to mean the introduction of foreign DNA into a host cell. This can be achieved for example by transformation, transfection or infection with an appropriate plasmid or viral vector using e.g. conventional techniques as described in Genetic Engineering; Eds. S. M. Kingsman and A. J. Kingsman; Blackwell Scientific Publications; Oxford, England, 1988. The term 'transformed' or 'transformant' will hereafter apply to the resulting host cell containing and expressing the foreign gene of interest.

The expression vectors are novel and also form part of the invention.

The replicable expression vectors may be prepared in accordance with the invention, by cleaving a vector compatible with the host cell to provide a linear DNA segment having an intact replicon, and combining said linear segment with one or more DNA molecules which, together with said linear segment encode the desired product, such as the DNA polymer encoding the Osp A protein, or derivative thereof, such as an NS1 Osp A-fusion protein under ligating conditions.

Thus, the DNA polymer may be preformed or formed during the construction of the vector, as desired.

The choice of vector will be determined in part by the host cell, which may be prokaryotic or eukaryotic. Suitable vectors include plasmids, bacteriophages, cosmids and recombinant viruses.

The preparation of the replicable expression vector may be carried out conventionally with appropriate enzymes for restriction, polymerisation and ligation of the DNA, by procedures described in, for example, Maniatis et al cited above.

The recombinant host cell is prepared, in accordance with the invention, by transforming a host cell with a replicable expression vector of the invention under transforming conditions. Suitable transforming conditions are conventional and are described in, for example, Maniatis et al cited above, or "DNA Cloning" Vol. II, D. M. Glover ed., IRL Press Ltd, 1985.

The choice of transforming conditions is determined by the host cell. Thus, a bacterial host such as *E. coli* may be treated with a solution of $CaCl_2$ (Cohen et al, Proc. Nat. Acad. Sci., 1973, 69, 2110) or with a solution comprising a mixture of RbCl, $MnCl_2$, potassium acetate and glycerol, and then with 3-[N-morpholino]-propane-sulphonic acid, RbCl and glycerol. Mammalian cells in culture may be transformed by calcium co-precipitation of the vector DNA onto the cells. The invention also extends to a host cell transformed with a replicable expression vector of the invention.

Culturing the transformed host cell under conditions permitting expression of the DNA polymer is carried out conventionally, as described in, for example, Maniatis et al and "DNA Cloning" cited above. Thus, preferably the cell is supplied with nutrient and cultured at a temperature below 50° C.

The product is recovered by conventional methods according to the host cell. Thus, where the host cell is bacterial, such as *E. coli* it may be lysed physically, chemically or enzymatically and the protein product isolated from the resulting lysate. Where the host cell is mammalian, the product may generally be isolated from the nutrient medium or from cell free extracts. Conventional protein isolation techniques include selective precipitation, adsorption chromatography, and affinity chromatography including a monoclonal antibody affinity column.

The proteins of the present invention when expressed in *E. coli* as full length proteins produce lipoprotein micelles which are immunogenic. Such full length lipoproteins form part of the present invention.

It will be appreciated that all the proteins of the present invention may find utility in vaccine and diagnostic applications.

Furthermore, it will be appreciated that other antigenic components such as other Osp A antigens or Osp B from *B. burgdorferi* isolates or antigens from other pathogens may be included in a vaccine composition of the present invention. Additionally other antigens from other organisms may be present in the vaccine.

The Osp A antigens utilised in the compositions of the present invention include immunogenic fragments of Osp A, i.e. fragments of Osp A containing immunogenic B or T-cell epitopes, or fusion proteins containing such epitopes, including fusions of Osp A's from different groups.

In an aspect of the present invention there is provided a vaccine or diagnostic composition comprising an Osp A or derivative thereof from a subgroup II strain. In particular one characterised in that it is encoded by a DNA sequence which will permit successful polymerase chain reaction to take place utilising prOsp A1–A4 primers, but not prOsp A1–A2, the protein being in admixture with suitable excipient or carrier. More particularly there is provided a composition comprising an Osp A or derivative thereof from a group II strain having an amino acid sequence substantially identical to the protein sequence depicted in sequence ID No.2.

Such compositions may advantageously also contain an Osp A derivative from a subgroup I strain.

Accordingly the present provides in a preferred embodiment a composition, preferably a vaccine composition comprising an Osp A antigen derived from a subgroup I *B. burgdorferi*, and an Osp A antigen from a subgroup II, *B. burgdorferi.*

Preferably the Osp A antigen from group I are selected from group, B31, ZS7 and N40.

Preferably the Osp A antigen from group II is selected from the group ZQ1, NE11H.

The present invention also provides a vaccine or diagnostic composition comprising an OspA or derivative from a subgroup III strain, the protein being a admixture with a suitable excipient or carrier. More particularly the vaccine or diagnostic composition comprises an OspA or derivative thereof having an amino acid sequence substantially identical to the protein sequence depicted in sequence ID No.4.

Preferably the OspA is derived from strain 19857.

The invention also provides a vaccine or diagnostic composition comprising an Osp A or derivative from subgroup IV, V or VI.

In a preferred embodiment there is provided a combination vaccine comprising at least two OspA's or derivatives thereof from different *B. burgdorferi* subgroups. Such vaccine compositions provide protection from a wider range of Borrelia infections than hitherto. Preferably the vaccine comprises an Osp A from each of groups I to IV and most preferably an Osp A from each of group I to VI.

In the vaccine of the invention, an aqueous solution of the protein(s) can be used directly. Alternatively, the protein, with or without prior lyophilization, can be mixed or absorbed with any of the various known adjuvants. Such adjuvants include, but are not limited to, aluminium hydroxide, muramyl dipeptide and saponins such as Quil A. Particularly preferred adjuvants are, MPL (monophosphoryl lipid A) and 3D-MPL (3Deacylated monophosphoryl lipid A). A further preferred adjuvant is known as QS21. 3 DMPL can be obtained by the methods disclosed in UK patent No. 2220211, whereas QS21 can be obtained by the method disclosed in U.S. Pat. No. 5,057,540. As a further exemplary alternative, the proteins can be encapsulated within microparticles such as liposomes or associated with oil in water emulsions. In yet another exemplary alternative, the proteins can be conjugated to an immuostimulating macromolecule, such as killed Bordetella or a tetanus toxoid.

The proteins of the present invention may be expressed by live vectors such as BCG, Listeria or Salmonella and formulated as live vaccines using such vectors.

Vaccine preparation is generally described in *New Trends and Developments in Vaccines,* Voller et al. (eds.), University Park Press, Baltimore, Md., 1978. Encapsulation within liposomes is described by Fullerton, U.S. Pat. No. 4,235,877. Conjugation of proteins to macromolecules is disclosed, for example, by Likhite, U.S. Pat. No. 4,372,945 and Armor et al., U.S. Pat. No. 4,474,757.

Use of Quil A is disclosed by Dalsgaard et al., *Acta Vet Scand*, 18:349 (1977). Use of 3D-MPL is described by Ribi et al. Microbiology (1986) LEVIE et al. (Eds) American Soc. for Microbiol. Wash. D.C. pp 9–13.

The amount of the protein of the present invention present in each vaccine dose is selected as an amount which induces an immunoprotective response without significant, adverse side effects in typical vaccines. Such amount will vary depending upon which specific immunogen is employed and whether or not the vaccine is adjuvanted. Generally, it is expected that each dose will comprise 1–1000 μg of protein, preferably 1–200 μg. An optimal amount for a particular vaccine can be ascertained by standard studies involving observation of antibody titres and other responses in subjects. Following an initial vaccination, subjects may receive an additional administration to enhance their immune response.

BRIEF DESCRIPTION OF THE DRAWING

FIG. 1 outlines the construction of three plasmids pOA-10, pOA-12 and pOA-18 used for expression of NS1-OspA fusion proteins.

EXAMPLE 1
Characteristics of *Borrelia burgdorferi* strain ZQ1

1.1. Isolation: Midgut sample of a female Ixodes ricinus captured in Freiburg-Kappel from a dog on May 31, 1988; grown in BSK supplemented with Kanamycin and Fluoruracil; culture became positive on Jun. 8, 1988; aliquots were frozen at −70° C. and in liquid nitrogen on Jun. 20, 1988.

In vitro passages usually used for experiments second and third of *B. burgdorferi* are used.

1.2 Cultivation: *Borrelia burgdorferi* strain ZQ1 is grown in Barbour-Stoenner-Kelly's medium as described for strain ZS7 (Schailble et al., J.Exp.Med. 170. 1989;). The generation time is around 30 to 40 hours (slower than strain ZS7; around 20–24 hours).

1.3 Plasmids: Plasmid analysis was done in parallel for strain ZQ1, ZS7, Z37, GeHo, and B31 according to the protocol of Barbour and Garon (1977): Plasmids with a molecular weight of 49, 29, 25, 20, 18 Kb and a faint band at 14 Kb are found in strain ZQ1. The 49 and 25 Kb plasmids are also present in B31, Z37, GeHo and ZS7, whereas the 29 and 20 Kb plasmids are only detectable in ZS7. The 18 and 14 Kb plasmids seem to be unique to ZQ1. The 16 Kb plasmid which is found in the other strains tested is lacking in ZQ1.

1.4 Polyacrylamide gel electrophoresis: There is a distinct pattern of proteins in strain ZQ1 when compared to other strains as revealed by polyacrylamide gel electrophoresis and silverstaining; there is no band in the range of 34 kDa (Osp B); the band most probably representing Osp A has a molecular weight of around 32 kDa. The corresponding band in the other strains (ZS7, Z37, GeHo, B31) migrates at 31 kDa.

1.5 Western Blot analysis: monoclonal antibodies (mAbs) to *Borrelia burgdorferi* (B31, GeHo) were used, ZQ1 shows a staining pattern distinct to that of the strains ZS7 and B31; there is no staining with any of the Osp A specific mAbs with the exception of the Osp A specific mAb LA- 31.1 which reacts with a corresponding band of molecular mass range around 32 kDa. None of the mAbs specific for Osp B of B31, ZS7 react with a protein of ZQ1. There is also no staining with the mAb LA.7 to a 20 kDa antigen. mAbs specific for the 65 kDa and the 70 kDa antigens stain structures in ZQ1 corresponding to those in other strains.

Immune Sera

The ZQ1 derived 32 kDa protein (Osp A) is recognized by rabbit Immune sera (IS) to *Borrelia burgdorferi* B31, mouse IS to *Borrelia burgdorferi* B1 and mouse IS *Borrelia burgdorferi* ZS7. There is no staining in the range of 34 kDa, IS to *Borrelia burgdorferi* ZQ1 reacts with Osp A, flagellin and a 20 (faint band), 50 and 65 (faint band) kDa band but not with Osp B of strain ZS7.

EXAMPLE 2

2.1 DNA Preparation and PCR Amplification

*B. burgdorferi* cells are lysed using the detergent SDS and proteins are removed by digestion with the nonspecific serine protease, proteinase K. Cell wall debris, polysaccharides, and remaining proteins are removed by selective precipitation with CTAB (cetyltrimethylammonium bromide), and DNA is recovered from the resulting supernatant by isopropanol precipitation. Briefly, spirochetes ($10^{10}$ cells) are washed in PBS and suspended in 9 ml TE. After addition of 1 ml SDS (20%) and 50 $\mu$l proteinase K (20 mg/ml), the solution was incubated for 1 hr at 37° C. Finally, 1.5 ml 5M NaCl and 1.25 ml CTAB (20% in 0.7 M NaCl) were added and the mixture was kept for 10 min. at 65° C. DNA was purified by phenol and chloroform/isoamylalcohol extration and subsequently precipitated with 0.6 vol. isopropanol for 10 min. at room temperature. The pellet was washed using 70% ethanol, dried and dissolved in TE. (10 mM Tris 0.1 mol EDTA pH 7.4).

Oligonucleotide primers for the polymerase chain reaction were chemically synthesized by using an Applied Biosystems (ABI) DNA synthesizer and b-cyanoethyl chemistry. The following sequences of oligonucleotides were used throughout the experiments:

```
prOsp A1: 5'-GGGAATAGGT CTAATATTAG CC-3';
prOsp A2: 5'-TGACCTGAATT CCAAGCTGCA-3';
prOsp A4: 5'-GCAGTTAAAG TTCCTTCAAG AACATAGC-3'.
```

Taq DNA polymerase and PCR reagents (Perkin Elmer-Cetus, Norwalk, Conn.) were used per 50 $\mu$l reaction. Each polymerase chain reaction contained 800 mM deoxynucleoside triphosphate, 2 U Taq DNA polymerase, 1.5 mM $MgCl_2$, and 0.5 mM of each primer. Routinely, 10 ng of total genomic *B. burgdorferi* DNA was amplified for 35 cycles under the following conditions: 94° C. for 1.2 min; 42° C. for 2 min; 72° C. for 2 min. A total of 10 $\mu$l per reaction was analysed on 1.5% agarose gels under standard electrophoresis conditions.

2.2 Southern Analysis

Total genomic *B. burgdorferi* DNA (20 $\mu$g), was digested with restriction enzymes as indicated, separated by electrophoresis on a 0.8% agarose gel, and transferred to nylon membrane (Hybond-N, Amersham). Blots were hybridized at 60° C. in Church-buffer (0.5M Na $HPO_4$ 17% $NaDodSO_4$, PH 7.2) over night with an Osp A (strain ZS7) probe labelled with $^{32}P$ by random primer extension and washed at 55° C. in 0.1×SSC/0.1% SDS.

Results

Table 1: Genotypical and phenotypical analyses of *B. burgdorferi* strains as analysed by PCR, and Southern blotting are shown in Table I.

Restriction Fragment Length Polymorphism of the Plasmid Encoded Osp A Gene

RFPL for Osp A using HindIII revealed at least six distinct hybridization patterns among the *B. burgdorferi* isolates tested. All of the *B. burgdorferi* strains tentatively termed as group A,A,A (for a fla, HSP60, HSP70) are characterized by two hybridization fragments of 1.2 kb and 0.3 kb (B31, ZS7; Osp A type I) and the majority of group B,B,B (for fla, HSP60, HSP70) strains (17/25) expressed two fragments of 0.9 kb and 0.4 kb (ZQ1; Osp A type II). *B. burgdorferi* strains 19857 and 21038 (group II,A/BA for fla, HSP60, HSP70) exhibited two hybridizing fragments of 4 kb and 0.5 kb (Osp A genotype III) and all ACA-1 like strains (group II,BA) express only one fragment of about 1.7 kb (Osp A type IV). Strains 20047 and S90 (group II,B,B) exhibit one fragment of 3 kb (Osp A type V) and 1.1 kb (Osp A type VI), respectively (Tables 1). DNAs' isolated from members of other species of Borrelia did not hybridize to the Osp A-specific probe. The frequencies of the individual OspA genotypes among B. burgdorferi isolates tested are: 30/55 (55%) Osp A type I. 17/55 (31%) type II, 2/55 (4%) type III, 4/55 (7%) type IV, 1/55 (2%) type V and 1/55 (2%) type VI. Note that American B. burgdorferi isolates analysed to this end belong to only one Osp A genotype, i.e. type I, with the exception of two strains, 19857 and 21038, which express Osp A genotype III; in contrast, among European isolates five Osp A genotypes, i.e. I, II, IV, V and VI are found. The results are summarised in table IV.

EXAMPLE 3

Pathogenicity: Inoculation of scid mice with $10^8$ ZQ1 subcutaneously in the tail leads to clinical arthritis around day 50 post inoculation. Histopathological alterations in the joints investigated at day 57 were comparable to those described for scid mice infected with strain ZS7 in earlier stages of the disease. ZQ1 is therefore less pathogenic than ZS7. Spirochetes could be isolated at day 57 post inoculation from scid mice infected with ZQ1.

When 5 C57BL/6 mice were inoculated with $10^8$ B.b. ZQ1 subcutaneously in the tail, only one mouse developed unilateral clinical arthritis at day 71 post inoculation within the entire observation period of 160 days.

EXAMPLE 4

Crossprotection: Reconstitution of scid mice with IS to ZQ1 (32 μg specific Ig/ml; 100 μl at days 0 and 4, 200 ml at days 7 and 11 and 300 μl at days 15 and 19) did not protect these mice against a challenge with ZS7 given at day 0.

EXAMPLE 5

Further crossprotection studies were carried out utilising strain the Group II strain NE11H and the group I ZS7. Transfer of immune sera into SCID mice as shown in Table II only protected against homologous challenge (i.e. challenge within the same group).

EXAMPLE 6

Crossprotection experiments using isolates or to immune sera to either various B. burgdorferi isolates or to rec.Osp A of strain ZS7
Materials and Methods
Methods Mice (C57BL/6 or DBA/2) were inoculated with $1\times10^8$ viable B. burgdorferi spirochetes of the strains ZS7 (IS anti-ZS7), ZQ1 (IS anti-ZQ1), NE11H (IS anti-NE11H), B31 (IS anti-B31) or a mixture containing equal amounts of strains 20047, ZS7, NE11H, 21305, 21038, 21343, 26816, 28691 and 19535 (IS anti-cocktail) subcutaneously (sc) into the basis of the tail.

Rec.Osp A from strain ZS7 was expressed from the pUEX1 expression vector in Escherichia coli, the proteins were extracted and affinity purified using an Osp A specific mab (LA-2). Mice were primed s.c. and boosted after 10 and 20 days with 10 μg rec. Osp A in adjuvant (ABM2; Sebac, Aidenbach, FRG).

Immune sera (IS) were obtained from these mice by several bleedings between week three and ten post inoculation (p.i.). SCID mice were injected intraperitoneally (i.p.) with IS either once (60 μg B. burgdorferi specific Ig; IS anti-ZS7, IS anti-NE11H, IS anti-cocktail, IS anti rec. Osp A) one hour before inoculation or six times for three weeks (IS anti-B31 containing 60 μg/ml specific Ig; IS anti-ZQ1 containing 32 μg/ml) with increasing amounts of antibodies (100 μl day 1 and 4, 200 μl day 7 and 11,300 μl day 14 and 17 p.i.). SCID mice were inoculated with $1\times10^8$ viable B. burgdorferi spirochetes of the strains ZS7, SH-2-82-P5, 21038, NE11H or 20047 s.c. into the base of the tail one hour after the (first) transfer of serum.
Results Immune sera to subgroup I strains ZS7 and B31 protect against homologous challenge, only partially against heterologous challenge with strain 20047 (subgroup V) and not at all against heterologous challenge with subgroup II strain NE11H. Immune sera to group II strain NE11H only partially protects against heterologous challenge with strain 20047 (subgroup V) and not at all against heterologous challenge with strain ZS7 (subgroup I).

Pretreatment of SCID mice with monospecific anti-rec. Osp A (ZS7) IS resulted in protection against development of disease when challenged with either strain ZS7 (2/6) or SH-2-82-P5 (2/3; flaA, OspA/OspB I) and in partial protection when challenged with 20047 (1/3; flab, Osp A/Osp B V) or 21038 (2/3; fla B, Osp A/Osp B III; Table 2). The clinical arthritis observed in the majority of these mice under these conditions was only mild. In contrast, SCID mice treated with the same IS to rec. Osp A but subsequently challenged with NE11H (fla B, Osp A/Osp B II) were not protected at all. All of these mice developed clinical arthritis (3/3) comparable to that seen in infected and otherwise untreated SCID mice (Table 3).

EXAMPLE 7
Construction of Expression Plasmids Encoding NS1-OspA (ZS7) Fusion

FIG. 1 outlines the construction of the three plasmids pOA-10, POA-12 and pOA-18.

Briefly, pOA-10 was created in three steps. First, a 1.1 kb NspH 1 fragment of pZS7-2 (Dr Wallich) containing the truncated OspA 'gene was ligated, after trimming of the protruding ends, with pUC19 linearized with Sma 1. In the resulting plasmid, named pOA-5, the OspA gene is flanked by various unique restriction sites,(in 5' end these are Hind III, Sph I, Pst I Sal I, Xba and BamH I and in the 3' end Sac 1 and EcoR I) making easier its subcloning. Secondly, pOA-5 was linearized by Xba I and ligated with pMG42 linearized by BamH I, after fill-in of the ends of both fragments to create pOA-9. The portion of this plasmid derived from pUC 19 has subsequently been removed by an Nco I digestion, generating pOA-10. In this plasmid, the truncated OspA gene is in frame with the first codon of NS1. The junction at the 5' end of the insert has been verified by sequencing. To create pOA-12 and pOA-18, we generated Nco I and Xba I restriction sites respectively at the 5' and the 3' ends of the DNA fragment coding for the truncated OspA gene using polymerase chain reaction (PCR). After digestion with Nco I and Xba I, this fragment was ligated with pMG42 or TCM67 digested with the same enzymes to obtain respectively pOA-12 and pOA-18. The first plasmid pOA-12, expresses the truncated OspA gene fused to the first 42 amino acids, the latter, pOA-18, to the first 81 amino acids of NS1. The insert of both plasmids have been sequenced to verify that no amino acid substitution has been introduced in OspA gene during the PCR.

All three plasmids have been transformed into E. coli AR120 which allows the induction the λpL promoter by the addition of nalidixic acid. Additionally all three plasmids have been transformed into E. coli AR58 which allows induction of the λpL promoter by an increase in temperature.

EXAMPLE 8

Expression of Recombinant trOspA from pOA-10, pOA-12 and POA-18

Fifty ml cultures (LB medium supplemented with the appropriate antibiotics) of the three strains AR120 (pOA-10), AR120 (pOA-12) and AR120 (pOA-18) were inoculated with 0.25 ml of an overnight preculture and grown at 37° C. At an $A_{620}$ of about 0.3, the cells contained in 5 ml of culture have been harvested and resuspended in SDS sample buffer. Nalidixic acid has been added to the remaining culture to a final concentration of 60 mg/ml. Three hours later the cells from the 5 ml cultures were harvested and resuspended in SDS sample buffer.

In parallel to the three AR120 strains, JM109 and JM109 (pZS7-2) strains have been grown in 50 ml of LB medium up to an optical density (620 nm) of 0.6 and treated as described above. In JM109(pZS7-2), the native form of OspA is expressed constitutively from its own promoter. All samples were submitted to SDS-PAGE and Western blot analysis using a pool of the mAbs LA-2, LA-26, and LA-31 to detect the OspA derivatives.

Analysis of samples corresponding to uninduced and induced cells (in the case of pZS7-2, host without and with the plasmid), were carried out. The amount of material loaded into each well was standarized on the basis of the optical density of the cultures (0.05 $A_{620}$/well). On the stained gel, in the lane induced of JM109(pZS7-2) and of induced AR120(pOA-18), new bands appear which migrations are consistent with the expected size of the products to be expressed (respectively native OspA and trOspA fused to 81 amino acids of NS1). Native OspA appears as a doublet and it represents a few percents of the total protein content of the bacteria. The product of pOA-18 is expressed at higher level than the native protein. The Western blot analysis confirms that these new bands correspond to OspA derivatives. The blot further shows that AR120(pOA-12) expresses trOspA fused with 42 amino acids of NS1 but at a lower level. The expression of trOspA from pOA-10 appears as a faint band, corresponding to the expected size of trOspA and was observed on Western blot.

Similar results have been observed when the same plasmids are introduced into E. coli AR58 and the expression of the Osp A gene derivative induced by an increase of temperature. Also we have obtained similar $NS1_{1-81}$ Osp A ZS7 fusion protein utilising a kanamycin resistance encoding plasmid.

EXAMPLE 9

Comparison of Cells Fractionation of AR120(pOA18) and JM109(pZS7-2)

E. coli strain AR120(pOA18) was grown, and the expression of the Osp A genes induced as described above.

E. coli strain JM109(pZS7-2), in which the native gene of Osp A is expressed constitutively from its own promoter, has been grown in 50 ml of LB medium supplemented with 100 μg/ml of ampicillin up to an optical density (620 nm) of 0.6.

The cells of both strains were then treated as follows. The cells contained in 5 ml have been harvested by centrifugation and resuspended in SDS-PAGE sample buffer (sample T3). The cells in the remaining 40 ml were harvested, washed twice in buffer A (Tris-HCl 50 mM, pH 7.5) and disrupted in the same buffer by two passages at 10,000 lb/in$^2$ through a French pressure cell. Cell homogenates were fractionated by centrifugation. The supernatants were stored at −20° C. (samples D3). The pellets were washed twice in buffer A and solubilized overnight in SDS-PAGE sample buffer at room temperature (sample C3). Results of the cell fractionation of the 2 expressing strains were analyzed by SDS-PAGE and Western blot was conducted as above except that only 0.025 $A_{620}$ Of "cell-equivalent" was loaded into each well. The native OspA, expressed in JM109(pZS7-2), is found in both the soluble (S3) and the insoluble (C3) cellular fractions. The lower band of the doublet is found preferentially in the insoluble fraction, while the upper band is almost entirely in the soluble fraction. The high molecular weight protein that appear only in the C3 lane of JM109 (pZS7-2) is not recognized by the anti-OspA antibodies and is thus probably not OspA-derived. On the other hand the product of pOA-18 is found almost exclusively in the soluble fraction.

EXAMPLE 10

Reactivity of NSI-OspA from pOA-18 with 4 anti-OspA mAbs

Crude cell extracts pf AR120 (pOA18) and JM109(pZS7-2) were prepared as described above. They were submitted to SDS-PAGE in four series of side by side wells (AR120 (pOA-18) and JM109(pZS7-2)) and their proteins transferred onto a nitrocellulose membrane. The membrane were then cut in four fragments each containing a pair of side by side lanes. Each fragment was submitted to a Western blot analysis with a different anti-Osp A mAb. The results indicate that the NSI-Osp A encoded by pOA-18 and the native Osp A react with all four monoclonals in a similar fashion.

EXAMPLE 11

In an analogous fashion to the construction of pOA-18, plasmids were constructed to express NS1-OspA fusions proteins from other B. burgdorferi strain. In particular the following fusion from the following strains were made and tested as noted above: NS1-OspA (ZQ1); NS1-OspA (AcaI) and NS1-OspA (19857).

Summary and Conclusions

A recombinant truncated form of OspA, lacking the 16 first amino acids of the native protein and fused to the first 81 amino acids of NS1, is expressed at a higher level than the native OspA. It is more soluble than the native protein and retains the reactivity with those monoclonal antibodies binding to the respective native Osp A is immunogenic when applied with adjuvants and has the ability to protect animals from challenge with virulent B. burgdorferi.

TABLE I

| Strain | Origin | Source | PCR aa 6-170 Osp A1–A4 | PCR aa 6-220 Osp A1–A2 | Southern Hind III* Osp A ( ) |
|---|---|---|---|---|---|
| B31 | USA | *Ixodes dammini* | + | + | I (A) |
| ZS7 | Germany | *I. ricinus* | + | + | I (A) |
| Z37 | Germany | *I. ricinus* | + | + | I (A) |
| GeHo | Germany | Skin (ECM) | + | + | I (A) |
| B1 | Germany | Human Skin Biopsy | + | + | I (A) |
| B2 | Germany | Human Skin Biopsy | + | + | I (A) |
| B3 | Germany | Human Skin Biopsy | + | + | I (A) |
| 20004 | France | *I. ricinus* | + | + | I (A) |
| 19535 | USA | *Peromyscus leucopus* | + | + | I (A) |
| 26816 | USA | Microtus+ | + | + | I (A) |
| 28691 | USA | *I. dammini* | + | + | I (A) |
| 21305 | USA | *Peromysous leucopus* | + | + | I (A) |
| 21343 | USA | *Peromysous leucopus* | + | + | I (A) |
| 26815 | USA | Chipmunk | + | + | I (A) |
| R7NE4 | Switzerland | *I. ricinus* | + | + | I (A) |
| 297 | USA | Human/Spinal fluid | + | + | I (A) |
| MAC3 | USA | Human | + | + | I (A) |
| 20001 | France | *I. ricinus* | + | + | I (A) |
| CT1P7 | USA | Tick Isolate/dog | + | + | I (A) |
| SH-2-82-P5 | USA | *I. dammini* | + | + | I (A) |
| CA-2-87 | USA | *I. pacificus* | n.d. | n.d. | I (A) |
| S12/14 | Germany | *I. ricinus* | + | + | I (A) |
| 19857 | USA | Rabbit Kidney | + | – | III (C) |
| ZQ1 | Germany | *I. ricinus* | + | – | II (B) |
| NE4 | Switzerland | *I. ricinus* | + | – | II (B) |
| NE58 | Switzerland | *I. ricinus* | + | – | II (B) |
| NE11H | Switzerland | *I. ricinus* | + | n.d. | II (B) |
| R7NE58 | Switzerland | *I. ricinus* | + | n.d. | II (B) |
| 20047 | France | *I. ricinus* | + | – | II (B) |
| N34 | Germany | *I. ricinus* | + | – | II (B) |
| 21038 | USA | *I. dentatus* | + | – | III (C) |
| ACA-1 | Sweden | Human skin | – | – | IV (D) |
| 20047 | France | *I. ricinus* | n.d. | n.d. | V (E) |
| S90 | Germany | *I. ricinus* | n.d. | n.d. | VI (F) |

*alternative nomenclature
I Osp A genotype

TABLE II

| immune serum transferred anti- | Crossprotection strain inoculated | protection (no arthritis) |
|---|---|---|
| ZS7 | ZS7 | + |
| ZS7 | NE11H | – |
| NE11H | NE11H | + |
| NE11H | ZS7 | – |
| NE11H | 20047° | ± |
| NE11H | 19857° | ± |
| ZS7 | 20047° | ± |
| IS cocktail* | 19857° | + |
| IS cocktail* | 19857° | ± |

*including 20047, ZS7 and NE11H;
°strains showed reduced pathogenicity in unprotected controls.

TABLE III

| immune serum transferred anti- | strain inoculated | Crossprotection clinical arthritis d23–25 p.i. | protection histo-pathology+ | spiro-chetemia§ |
|---|---|---|---|---|
| — | ZS7 | 8/8 | + | 5/7 |
| ZS7 | ZS7 | 0/3 | – | 0/3 |
| ZS7 | NE11H | 3/3 | + | 3/3 |
| ZS7 | 20047 | (2/3)° | ± | 3/3 |
| B31 | ZS7 | 0/3 | – | 3/3 |
| — | NE11H | 7/7 | + | 4/5 |
| NE11H | NE11H | (2/6)° | –^ | 0/6 |
| NE11H | ZS7 | 3/3 | + | 3/3 |
| NE11H | 20047 | (2/3)° | ± | 1/3 |
| ZQ1 | ZS7 | 3/3 | + | 3/3 |
|  | 20047 | 4/4 | + | 2/3 |
| IS cocktail* | 20047 | 0/3 | –^ | 1/3 |
| rec.OspA (ZS7) | ZS7 | (2/6)° | – | 5/6 |
| rec.OspA (ZS7) | NE11H | 3/3 | + | 2/3 |
| rec.OspA(ZS7) | 20047 | (1/3)° | ± | 0/2 |
| — | SH-2-82-P5 | 2/2 | + | 1/2 |

TABLE III-continued

| | | Crossprotection | | |
|---|---|---|---|---|
| immune serum transferred anti- | strain inoculated | clinical arthritis d23–25 p.i. | protection histo- pathology+ | spiro- chetemia§ |
| rec.OspA (ZS7) | SH-2-82-P5 | (2/3)° | −^ | 0/3 |
| — | 21038 | (2/2) | ± | 1/2++ |
| rec.OspA (ZS7) | 21038 | (2/3)° | −^ | 0/2 |

Legend: Table III: Crossprotection
*including *B. burgdoferi* organisms of strains 20047, ZS7 and NE11H;
+arthritis, carditis, hepatitis, myositis
°only, mild clinical arthritis
^only minor histopathological alterations
§recultivation
++non-motile spirochaetes

TABLE IV

| *B. burgdorferi* isolate | Biological origin | Geographical origin | fla/HSP60/HSP70 genogroup | OspA genotype |
|---|---|---|---|---|
| B31 (ATCC35210) | Tick (*I. dammini*) | USA | A/A/A | I |
| ZS7 | Tick (*I. ricinus*) | Germany | A/A/A | I |
| Z37 | Tick (*I. ricinus*) | Germany | A/A/A | I |
| GeHo | Skin (ECM) | Germany | A/A/A | I |
| B1 | Skin (ECM) | Germany | A/A/A | I |
| B2 | Skin (ECM) | Germany | A/A/A | I |
| B3 | Skin (AD) | Germany | A/A/A | I |
| 20004 | Tick (*I. ricinus*) | France | A/A/A | I |
| 19535 | Mouse (Peromyscus) | USA | A/A/A | I |
| 26816 | Vole (Microtus) | USA | A/A/A | I |
| 28691 | Tick (*I. dammini*) | USA | A/A/A | I |
| 21305 | Mouse (Peromyscus) | USA | A/A/A | I |
| 21343 | Mouse (Peromyscus) | USA | A/A/A | I |
| 26815 | Chipmunk | USA | A/A/A | I |
| 297 | Cerebrospinal fluid | USA | A/A/A | I |
| Mac3 | Skin | USA | A/A/A | I |
| 20001 | Tick (*I. ricinus*) | France | A/A/A | I |
| CTIP7 | Dog tick | USA | A/A/A | I |
| SH-2-92-P5 | Tick (*I. dammini*) | USA | A/A/A | I |
| CA-2-87 | Tick (*I. pacificus*) | USA | A/A/A | I |
| S12/14 | Tick (*I. ricinus*) | Germany | A/A/A | I |
| Z25 | Tick (*I. ricinus*) | Germany | A/A/A | I |
| Z118 | Tick (*I. ricinus*) | Germany | A/A/A | I |
| Z136 | Tick (*I. ricinus*) | Germany | A/A/A | I |
| Z160 | Tick (*I. ricinus*) | Germany | A/A/A | I |
| IP1 | Cerebrospinal fluid | France | A/A/A | I |
| NE2 | Tick (*I. ricinus*) | Switzerland | A/A/A | I |
| R7NE4 | Tick (*I. ricinus*) | Switzerland | A/A/A | I |
| LW2 | Skin | Germany | A/A/A | I |
| LW2.4 | Skin | Germany | A/A/A | I |
| 19857 | Rabbit Kindey | USA | B/A/B/A | III |
| 21038 | Larva (*I dentatus*) | USA | B/A/B/A | III |
| ACA-1 | Skin (ACA) | Sweden | B/B/A | IV |
| Bo23 | Skin (ECM) | Germany | B/B/A | IV |
| So2 | Tick (*I. ricinus*) | Great Britain | B/B/A | IV |
| PKo | Skin (ECM) | Germany | B/B/A | IV |
| ZQ1 | Tick (*I. ricinus*) | Germany | B/B/B | II |
| NE4 | Tick (*I. ricinus*) | Switzerland | B/B/B | II |
| NE58 | Tick (*I. ricinus*) | Switzerland | B/B/B | II |
| NE11H | Tick (*I. ricinus*) | Switzerland | B/B/B | II |
| R3NE2 | Tick (*I. ricinus*) | Switzerland | B/B/B | II |
| N34 | Tick (*I. ricinus*) | Germany | B/B/B | II |
| IP3 | Cerebrospinal fluid | France | B/B/B | II |
| IRS Us | | Germany | B/B/B | II |
| Frst1 | Skin | Germany | B/B/B | II |
| Frst2 | Skin | Germany | B/B/B | II |
| So1 | Tick (*I. ricinus*) | Great Britain | B/B/B | II |
| 42/87 | | Sweden | B/B/B | II |
| 152/86 | | Sweden | B/B/B | II |
| MK5 | Tick (*I. ricinus*) | Hungary | B/B/B | II |
| MK6 | Tick (*I. ricinus*) | Hungary | B/B/B | II |

TABLE IV-continued

| B. burgdorferi isolate | Biological origin | Geographical origin | fla/HSP60/HSP70 genogroup | OspA genotype |
| --- | --- | --- | --- | --- |
| 387 | Cerebrospinal fluid | Germany | B/B/B | II |
| 50 | Cerebrospinal fluid | Germany | B/B/B | II |
| 20047 | Tick (I. ricinus) | France | B/B/B | V |
| S90 | Tick (I. ricinus) | Germany | B/B/B | VI |

We claim:

1. A vaccine comprising at least two purified OspA proteins from different *Borrelia burgdorferi* subgroups wherein at least two of said purified OspA proteins are selected from the group consisting of: subgroup I, subgroup II, subgroup III, subgroup IV, subgroup V and subgroup VI.

2. The vaccine of claim 1 wherein one OspA protein of the *Borrelia burgdorferi* subgroups is from subgroup II.

3. The vaccine of claim 2 wherein the (strain) OspA protein of *Borrelia burgdorferi* subgroup is ZQ1 or NE11H.

4. The vaccine of claim 2 wherein the OspA protein of subgroup II is the sequence as set forth in SEQ ID No:2.

5. The vaccine of claim 1 wherein the *Borrelia burgdorferi* subgroups comprise subgroup I and subgroup II.

6. The vaccine of claim 5 wherein the (strain) OspA protein of *Borrelia burgdorferi* subgroup I is B31, ZS7 or N40.

7. The vaccine of claim 5 which comprises *Borrelia burgdorferi* strain ZS7 from subgroup I and *Borrelia burgdorferi* strain ZQ1 from subgroup II.

8. The vaccine of claim 1 wherein the *Borrelia burgdorferi* subgroups comprise subgroup I, subgroup II and subgroup IV.

9. The vaccine of claim 8 wherein the (strain) OspA protein of *Borrelia burgdorferi* subgroup IV is ACA-1.

10. The vaccine of claim 1 wherein *Borrelia burgdorferi* subgroups comprise subgroup I, subgroup II, subgroup III and subgroup IV.

11. The vaccine of claim 10 wherein the OspA protein of subgroup III is the sequence as set froth in SEQ ID No:4.

12. The vaccine of claim 1 comprising NS1-OspA fusion proteins in admixture with a suitable carrier.

13. A method to protect against infection by two or more *Borrelia burgdorferi* subgroups comprising administering an immunologically effective amount of the vaccine of claim 1.

14. An OspA protein containing the amino acid sequence sat forth in SEQ ID No:4.

15. A method of treating a mammal susceptible to infection by *B. bargdorferi* comprising administering an immunologically effective amount of the protein as claimed in claim 14.

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 825 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: BORRELIA BURGDORFERI
        (B) STRAIN: ZQ1

(xi) SEQUENCE DESCRIPTION: SEQ ID NO:1:

```
ATGAAAAAAT ATTTATTGGG AATAGGTCTA ATATTAGCCT TAATAGCATG TAAGCAAAAT      60
GTTAGCAGCC TTGATGAAAA AAATAGCGTT TCAGTAGATT TACCTGGTGG AATGAAAGTT     120
CTTGTAAGTA AAGAAAAAGA CAAAGATGGT AAATACAGTC TAGAGGCAAC AGTAGACAAG     180
CTTGAGCTTA AAGGAACTTC TGATAAAAAC AACGGTTCTG AACACTTGA AGGTGAAAAA      240
ACTGACAAAA GTAAAGTAAA ATTAACAATT GCTGAGGATC TAAGTAAAAC CACATTTGAA     300
ATTTTCAAAG AAGATGGCAA AACATTAGTA TCAAAAAAAG TAACCCTTAA AGACAAGTCA     360
TCAACAGAAG AAAAATTCAA CGAAAAGGGT GAAATATCTG AAAAAACAAT AGTAAGAGCA     420
AATGGAACCA GACTTGAATA CACAGACATA AAAAGCGATG GATCCGGAAA AGCTAAAGAA     480
GTTTTAAAAG ACTTTACTCT TGAAGGAACT CTAGCTGCTG ACGGCAAAAC AACATTGAAA     540
GTTACAGAAG GCACTGTTGT TTTAAGCAAG AACATTTTAA AATCCGGAGA AATAACAGTT     600
GCACTTGATG ACTCTGACAC TACTCAGGCT ACTAAAAAAA CTGGAAAATG GGATTCAAAG     660
ACTTCCACTT TAACAATTAG TGTGAATAGC CAAAAAACCA AAAACCTTGT ATTCACAAAA     720
GAAGACACAA TAACAGTACA AAAATACGAC TCAGCAGGCA CCAATCTAGA AGGCAAAGCA     780
GTCGAAATTA CAACACTTAA AGAACTTAAA GACGCTTTAA AATAA                    825
```

(2) INFORMATION FOR SEQ ID NO:2:

(i) SEQUENCE CHARACTERISTICS:
        (A) LENGTH: 274 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: BORRELIA BURGDORFERI
        (B) STRAIN: ZQ1

(xi) SEQUENCE DESCRIPTION: SEQ ID NO:2:

```
Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
             20                  25                  30

Asp Leu Pro Gly Gly Met Lys Val Leu Val Ser Lys Glu Lys Asp Lys
         35                  40                  45

Asp Gly Lys Tyr Ser Leu Glu Ala Thr Val Asp Lys Leu Glu Leu Lys
 50                  55                  60

Gly Thr Ser Asp Lys Asn Asn Gly Ser Gly Thr Leu Glu Gly Glu Lys
 65                  70                  75                  80

Thr Asp Lys Ser Lys Val Lys Leu Thr Ile Ala Glu Asp Leu Ser Lys
                 85                  90                  95

Thr Thr Phe Glu Ile Phe Lys Glu Asp Gly Lys Thr Leu Val Ser Lys
             100                 105                 110

Lys Val Thr Leu Lys Asp Lys Ser Ser Thr Glu Glu Lys Phe Asn Glu
         115                 120                 125

Lys Gly Glu Ile Ser Glu Lys Thr Ile Val Arg Ala Asn Gly Thr Arg
 130                 135                 140

Leu Glu Tyr Thr Asp Ile Lys Ser Asp Gly Ser Gly Lys Ala Lys Glu
145                 150                 155                 160

Val Leu Lys Asp Phe Thr Leu Glu Gly Thr Leu Ala Ala Asp Gly Lys
                 165                 170                 175

Thr Thr Leu Lys Val Thr Glu Gly Thr Val Val Leu Ser Lys Asn Ile
             180                 185                 190

Leu Lys Ser Gly Glu Ile Thr Val Ala Leu Asp Asp Ser Asp Thr Thr
         195                 200                 205

Gln Ala Thr Lys Lys Thr Gly Lys Trp Asp Ser Lys Thr Ser Thr Leu
 210                 215                 220

Thr Ile Ser Val Asn Ser Gln Lys Thr Lys Asn Leu Val Phe Thr Lys
225                 230                 235                 240

Glu Asp Thr Ile Thr Val Gln Lys Tyr Asp Ser Ala Gly Thr Asn Leu
                 245                 250                 255

Glu Gly Lys Ala Val Glu Ile Thr Thr Leu Lys Glu Leu Lys Asp Ala
             260                 265                 270

Leu Lys
```

(2) INFORMATION FOR SEQ ID NO:3:

(i) SEQUENCE CHARACTERISTICS:
        (A) LENGTH: 819 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: BORRELIA BURGDORFERI
        (B) STRAIN: 19857

(xi) SEQUENCE DESCRIPTION: SEQ ID NO:3:

```
ATGAAAAAAT ATTTATTGGG AATAGGTCTA ATATTAGCCT TAATAGCATG TAAGCAAAAT    60

GTTAGCAGCC TTGACGAGAA AAACAGCGTT TCAGTAGATG TACCTGGTGG AATGAAAGTT   120

CTTGTAAGCA AAGAAAAAAA CAAAGACGGC AAGTACGATC TAATGGCAAC AGTGGACAAC   180
```

-continued

```
GTTGATCTTA AAGGAACTTC TGACAAAAAC AATGGATCTG GAATACTTGA AGGCGTAAAA      240

GCTGATAAAA GTAAAGTAAA ATTAACAGTT GCTGACGATC TAAGCAAAAC CACACTTGAA      300

GTTTTAAAAG AAGATGGTAC AGTAGTGTCA AGAAAAGTAA CTTCCAAAGA CAAGTCAACA      360

ACAGAAGCAA AATTCAACGA AAAAGGTGAA TTGTCTGAAA AACAATGAC AAGAGCAAAC       420

GGAACTACTC TTGAATACTC ACAAATGACA AATGAAGACA ATGCTGCAAA AGCAGTAGAA      480

ACTCTTAAAA ACGGCATTAA GTTTGAAGGA AATCTCGCAA GTGGAAAAAC AGCAGTGGAA      540

ATTAAAGAAG GCACTGTTAC TCTAAAAAGA GAAATTGATA AAAATGGAAA AGTAACCGTC      600

TCTTTAAATG ACACTGCATC TGGTTCTAAA AAAACAGCTT CCTGGCAAGA AAGTACTAGC      660

ACCTTAACAA TTAGTGCAAA CAGCAAAAAA ACTAAAGATC TAGTGTTCCT AACAAACGGT      720

ACAATTACAG TACAAAATTA TGACTCAGCT GGCACTAAAC TTGAAGGATC AGCAGCTGAA      780

ATTAAAAAAC TCGATGAACT TAAAAACGCT TTAAGATAA                             819
```

(2) INFORMATION FOR SEQ ID NO:4:

(i) SEQUENCE CHARACTERISTICS:
        (A) LENGTH: 272 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: BORRELIA BURGDORFERI
        (B) STRAIN: 19857

(xi) SEQUENCE DESCRIPTION: SEQ ID NO:4:

```
Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
            20                  25                  30

Asp Val Pro Gly Gly Met Lys Val Leu Val Ser Lys Glu Lys Asn Lys
        35                  40                  45

Asp Gly Lys Tyr Asp Leu Met Ala Thr Val Asp Asn Val Asp Leu Lys
    50                  55                  60

Gly Thr Ser Asp Lys Asn Asn Gly Ser Gly Ile Leu Glu Gly Val Lys
65                  70                  75                  80

Ala Asp Lys Ser Lys Val Lys Leu Thr Val Ala Asp Asp Leu Ser Lys
                85                  90                  95

Thr Thr Leu Glu Val Leu Lys Glu Asp Gly Thr Val Val Ser Arg Lys
            100                 105                 110

Val Thr Ser Lys Asp Lys Ser Thr Thr Glu Ala Lys Phe Asn Glu Lys
        115                 120                 125

Gly Glu Leu Ser Glu Lys Thr Met Thr Arg Ala Asn Gly Thr Thr Leu
    130                 135                 140

Glu Tyr Ser Gln Met Thr Asn Glu Asp Asn Ala Ala Lys Ala Val Glu
145                 150                 155                 160

Thr Leu Lys Asn Gly Ile Lys Phe Glu Gly Asn Leu Ala Ser Gly Lys
                165                 170                 175

Thr Ala Val Glu Ile Lys Glu Gly Thr Val Thr Leu Lys Arg Glu Ile
            180                 185                 190

Asp Lys Asn Gly Lys Val Thr Val Ser Leu Asn Asp Thr Ala Ser Gly
        195                 200                 205

Ser Lys Lys Thr Ala Ser Trp Gln Glu Ser Thr Ser Thr Leu Thr Ile
```

```
           210            215             220
Ser Ala Asn Ser Lys Lys Thr Lys Asp Leu Val Phe Leu Thr Asn Gly
225             230             235             240

Thr Ile Thr Val Gln Asn Tyr Asp Ser Ala Gly Thr Lys Leu Glu Gly
                245             250             255

Ser Ala Ala Glu Ile Lys Lys Leu Asp Glu Leu Lys Asn Ala Leu Arg
        260             265             270
```

(2) INFORMATION FOR SEQ ID NO:5:

(i) SEQUENCE CHARACTERISTICS:
        (A) LENGTH: 1020 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: BORRELIA BURGDORFERI
        (B) STRAIN: zq1

(vii) IMMEDIATE SOURCE:
        (B) CLONE: NS1-ZQ1

(xi) SEQUENCE DESCRIPTION: SEQ ID NO:5:

```
ATGGATCCAA ACACTGTGTC AAGCTTTCAG GTAGATTCCT TTCTTTGGCA TGTCCGCAAA     60
CGAGTTGCAG ACCAAGAACT AGGTGATGCC CCATTCCTTG ATCGGCTTCG CCGAGATCAG    120
AAATCCCTAA GAGGAAGGGG CAGCACTCTT GGTCTGGACA TCGAGACAGC CACACGTGCT    180
GGAAAGCAGA TAGTGGAGCG GATTCTGAAA GAAGAATCCG ATGAGGCACT TAAAATGACC    240
ATGGGAAAGC AAAATGTTAG CAGCCTTGAT GAAAAAAATA GCGTTTCAGT AGATTTACCT    300
GGTGGAATGA AAGTTCTTGT AAGTAAAGAA AAAGACAAAG ATGGTAAATA CAGTCTAGAG    360
GCAACAGTAG ACAAGCTTGA GCTTAAAGGA ACTTCTGATA AAACAACGG TTCTGGAACA    420
CTTGAAGGTG AAAAAACTGA CAAAAGTAAA GTAAAATTAA CAATTGCTGA GGATCTAAGT    480
AAAACCACAT TTGAAATTTT CAAAGAAGAT GGCAAAACAT TAGTATCAAA AAAAGTAACC    540
CTTAAAGACA AGTCATCAAC AGAAGAAAAA TTCAACGAAA AGGGTGAAAT ATCTGAAAAA    600
ACAATAGTAA GAGCAAATGG AACCAGACTT GAATACACAG ACATAAAAAG CGATGGATCC    660
GGAAAAGCTA AAGAAGTTTT AAAAGACTTT ACTCTTGAAG GAACTCTAGC TGCTGACGGC    720
AAAACAACAT TGAAAGTTAC AGAAGGCACT GTTGTTTTAA GCAAGAACAT TTTAAAATCC    780
GGAGAAATAA CAGTTGCACT TGATGACTCT GACACTACTC AGGCTACTAA AAAAACTGGA    840
AAATGGGATT CAAAGACTTC CACTTTAACA ATTAGTGTGA ATAGCCAAAA AACCAAAAAC    900
CTTGTATTCA CAAAAGAAGA CACAATAACA GTACAAAAAT ACGACTCAGC AGGCACCAAT    960
CTAGAAGGCA AAGCAGTCGA AATTACAACA CTTAAAGAAC TTAAAGACGC TTTAAAATAA   1020
```

(2) INFORMATION FOR SEQ ID NO:6:

(i) SEQUENCE CHARACTERISTICS:
        (A) LENGTH: 339 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: BORRELIA BURGDORFERI
        (B) STRAIN: ZQ1

(vii) IMMEDIATE SOURCE:
      (B) CLONE: NS1-ZQ1

(xi) SEQUENCE DESCRIPTION: SEQ ID NO:6:

Met Asp Pro Asn Thr Val Ser Ser Phe Gln Val Asp Ser Phe Leu Trp
1               5                   10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
            35                  40                  45

Thr Leu Gly Leu Asp Ile Glu Thr Ala Thr Arg Ala Gly Lys Gln Ile
50                  55                  60

Val Glu Arg Ile Leu Lys Glu Glu Ser Asp Glu Ala Leu Lys Met Thr
65                  70                  75                  80

Met Gly Lys Gln Asn Val Ser Ser Leu Asp Glu Lys Asn Ser Val Ser
            85                  90                  95

Val Asp Leu Pro Gly Gly Met Lys Val Leu Ser Lys Glu Lys Asp
            100                 105                 110

Lys Asp Gly Lys Tyr Ser Leu Glu Ala Thr Val Asp Lys Leu Glu Leu
            115                 120                 125

Lys Gly Thr Ser Asp Lys Asn Asn Gly Ser Gly Thr Leu Glu Gly Glu
            130                 135                 140

Lys Thr Asp Lys Ser Lys Val Lys Leu Thr Ile Ala Glu Asp Leu Ser
145                 150                 155                 160

Lys Thr Thr Phe Glu Ile Phe Lys Glu Asp Gly Lys Thr Leu Val Ser
            165                 170                 175

Lys Lys Val Thr Leu Lys Asp Lys Ser Ser Thr Glu Lys Phe Asn
            180                 185                 190

Glu Lys Gly Glu Ile Ser Glu Lys Thr Ile Val Arg Ala Asn Gly Thr
            195                 200                 205

Arg Leu Glu Tyr Thr Asp Ile Lys Ser Asp Gly Ser Gly Lys Ala Lys
            210                 215                 220

Glu Val Leu Lys Asp Phe Thr Leu Glu Gly Thr Leu Ala Ala Asp Gly
225                 230                 235                 240

Lys Thr Thr Leu Lys Val Thr Glu Gly Thr Val Val Leu Ser Lys Asn
            245                 250                 255

Ile Leu Lys Ser Gly Glu Ile Thr Val Ala Leu Asp Asp Ser Asp Thr
            260                 265                 270

Thr Gln Ala Thr Lys Lys Thr Gly Lys Trp Asp Ser Lys Thr Ser Thr
            275                 280                 285

Leu Thr Ile Ser Val Asn Ser Gln Lys Thr Lys Asn Leu Val Phe Thr
            290                 295                 300

Lys Glu Asp Thr Ile Thr Val Gln Lys Tyr Asp Ser Ala Gly Thr Asn
305                 310                 315                 320

Leu Glu Gly Lys Ala Val Glu Ile Thr Thr Leu Lys Glu Leu Lys Asp
            325                 330                 335

Ala Leu Lys (2) INFORMATION FOR SEQ ID NO:7:

(i) SEQUENCE CHARACTERISTICS:
        (A) LENGTH: 1014 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
             (A) ORGANISM: BORRELIA BURGDORFERI
             (B) STRAIN: 19857

(vii) IMMEDIATE SOURCE:
             (B) CLONE: NS1-19857

(xi) SEQUENCE DESCRIPTION: SEQ ID NO:7:

| | | | | | |
|---|---|---|---|---|---|
| ATGGATCCAA | ACACTGTGTC | AAGCTTTCAG | GTAGATTCCT | TTCTTTGGCA | TGTCCGCAAA | 60 |
| CGAGTTGCAG | ACCAAGAACT | AGGTGATGCC | CCATTCCTTG | ATCGGCTTCG | CCGAGATCAG | 120 |
| AAATCCCTAA | GAGGAAGGGG | CAGCACTCTT | GGTCTGGACA | TCGAGACAGC | CACACGTGCT | 180 |
| GGAAAGCAGA | TAGTGGAGCG | GATTCTGAAA | GAAGAATCCG | ATGAGGCACT | TAAAATGACC | 240 |
| ATGGGAAAGC | AAAATGTTAG | CAGCCTTGAC | GAGAAAAACA | GCGTTTCAGT | AGATGTACCT | 300 |
| GGTGGAATGA | AAGTTCTTGT | AAGCAAAGAA | AAAACAAAG | ACGGCAAGTA | CGATCTAATG | 360 |
| GCAACAGTGG | ACAACGTTGA | TCTTAAAGGA | ACTTCTGACA | AAAACAATGG | ATCTGGAATA | 420 |
| CTTGAAGGCG | TAAAAGCTGA | TAAAAGTAAA | GTAAAATTAA | CAGTTGCTGA | CGATCTAAGC | 480 |
| AAAACCACAC | TTGAAGTTTT | AAAAGAAGAT | GGTACAGTAG | TGTCAAGAAA | AGTAACTTCC | 540 |
| AAAGACAAGT | CAACAACAGA | AGCAAAATTC | AACGAAAAAG | GTGAATTGTC | TGAAAAAACA | 600 |
| ATGACAAGAG | CAAACGGAAC | TACTCTTGAA | TACTCACAAA | TGACAAATGA | AGACAATGCT | 660 |
| GCAAAAGCAG | TAGAAACTCT | TAAAAACGGC | ATTAAGTTTG | AAGGAAATCT | CGCAAGTGGA | 720 |
| AAAACAGCAG | TGGAAATTAA | AGAAGGCACT | GTTACTCTAA | AAAGAAAAT | TGATAAAAAT | 780 |
| GGAAAAGTAA | CCGTCTCTTT | AAATGACACT | GCATCTGGTT | CTAAAAAAAC | AGCTTCCTGG | 840 |
| CAAGAAAGTA | CTAGCACCTT | AACAATTAGT | GCAAACAGCA | AAAAAACTAA | AGATCTAGTG | 900 |
| TTCCTAACAA | ACGGTACAAT | TACAGTACAA | AATTATGACT | CAGCTGGCAC | TAAACTTGAA | 960 |
| GGATCAGCAG | CTGAAATTAA | AAAACTCGAT | GAACTTAAAA | ACGCTTTAAA | ATAA | 1014 |

(2) INFORMATION FOR SEQ ID NO:8:

(i) SEQUENCE CHARACTERISTICS:
             (A) LENGTH: 337 amino acids
             (B) TYPE: amino acid
             (C) STRANDEDNESS: single
             (D) TOPOLOGY: linear (ii) MOLECULE TYPE: protein (vi) ORIGINAL SOURCE:
             (A) ORGANISM: BORRELIA BURGDORFERI
             (B) STRAIN: 19857

(vii) IMMEDIATE SOURCE:
             (B) CLONE: NS1-19857

(xi) SEQUENCE DESCRIPTION: SEQ ID NO:8:

Met Asp Pro Asn Thr Val Ser Ser Phe Gln Val Asp Ser Phe Leu Trp
1               5                   10                  15

His Val Arg Lys Arg Val Ala Asp Gln Glu Leu Gly Asp Ala Pro Phe
                20                  25                  30

Leu Asp Arg Leu Arg Arg Asp Gln Lys Ser Leu Arg Gly Arg Gly Ser
            35                  40                  45

Thr Leu Gly Leu Asp Ile Glu Thr Ala Thr Arg Ala Gly Lys Gln Ile
        50                  55                  60

Val Glu Arg Ile Leu Lys Glu Glu Ser Asp Glu Ala Leu Lys Met Thr

```
         65                  70                  75                  80
Met Gly Lys Gln Asn Val Ser Ser Leu Asp Glu Lys Asn Ser Val Ser
                         85                  90                  95
Val Asp Val Pro Gly Gly Met Lys Val Leu Val Ser Lys Glu Lys Asn
                100                 105                 110
Lys Asp Gly Lys Tyr Asp Leu Met Ala Thr Val Asp Asn Val Asp Leu
            115                 120                 125
Lys Gly Thr Ser Asp Lys Asn Asn Gly Ser Gly Ile Leu Glu Gly Val
        130                 135                 140
Lys Ala Asp Lys Ser Lys Val Lys Leu Thr Val Ala Asp Asp Leu Ser
145                 150                 155                 160
Lys Thr Thr Leu Glu Val Leu Lys Glu Asp Gly Thr Val Val Ser Arg
                165                 170                 175
Lys Val Thr Ser Lys Asp Lys Ser Thr Thr Glu Ala Lys Phe Asn Glu
                180                 185                 190
Lys Gly Glu Leu Ser Glu Lys Thr Met Thr Arg Ala Asn Gly Thr Thr
            195                 200                 205
Leu Glu Tyr Ser Gln Met Thr Asn Glu Asp Asn Ala Ala Lys Ala Val
        210                 215                 220
Glu Thr Leu Lys Asn Gly Ile Lys Phe Glu Gly Asn Leu Ala Ser Gly
225                 230                 235                 240
Lys Thr Ala Val Glu Ile Lys Glu Gly Thr Val Thr Leu Lys Arg Glu
                245                 250                 255
Ile Asp Lys Asn Gly Lys Val Thr Val Ser Leu Asn Asp Thr Ala Ser
                260                 265                 270
Gly Ser Lys Lys Thr Ala Ser Trp Gln Glu Ser Thr Ser Thr Leu Thr
            275                 280                 285
Ile Ser Ala Asn Ser Lys Lys Thr Lys Asp Leu Val Phe Leu Thr Asn
        290                 295                 300
Gly Thr Ile Thr Val Gln Asn Tyr Asp Ser Ala Gly Thr Lys Leu Glu
305                 310                 315                 320
Gly Ser Ala Ala Glu Ile Lys Lys Leu Asp Glu Leu Lys Asn Ala Leu
                325                 330                 335
Lys
```

(2) INFORMATION FOR SEQ ID NO:9:

(i) SEQUENCE CHARACTERISTICS:
        (A) LENGTH: 1017 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: BORRELIA BURGDORFERI
        (B) STRAIN: ACA1

(vii) IMMEDIATE SOURCE:
        (B) CLONE: NS1-ACA1

(xi) SEQUENCE DESCRIPTION: SEQ ID NO:9:

```
ATGGATCCAA ACACTGTGTC AAGCTTTCAG GTAGATTCCT TCTTTGGCA TGTCCGCAAA      60

CGAGTTGCAG ACCAAGAACT AGGTGATGCC CCATTCCTTG ATCGGCTTCG CCGAGATCAG    120

AAATCCCTAA GAGGAAGGGG CAGCACTCTT GGTCTGGACA TCGAGACAGC CACACGTGCT    180

GGAAAGCAGA TAGTGGAGCG GATTCTGAAA GAAGAATCCG ATGAGGCACT TAAAATGACC    240
```

-continued

```
ATGGGAAAGC AAAATGTTAG CAGCCTTGAT GAAAAAAACA GCGCTTCAGT AGATTTGCCT      300

GGTGAGATGA AGTTCTTGT AAGTAAAGAA AAAGACAAAG ACGGTAAGTA CAGTCTAAAG       360

GCAACAGTAG ACAAGATTGA GCTAAAAGGA ACTTCTGATA AGACAATGG TTCTGGAGTG       420

CTTGAAGGTA CAAAGATGA CAAAAGTAAA GCAAAATTAA CAATTGCTGA CGATCTAAGT      480

AAAACCACAT TCGAACTTTT CAAGAAGAT GGCAAAACAT TAGTGTCAAG AAAAGTAAGT      540

TCTAAAGACA AACATCAAC AGATGAAATG TTCAATGAAA AAGGTGAATT GTCTGCAAAA      600

ACCATGACAA GAGAAAATGG AACCAAACTT GAATATACAG AAATGAAAAG CGATGGAACC      660

GGAAAAGCTA AGAAGTTTT AAAAAACTTT ACTCTTGAAG GAAAAGTAGC TAATGATAAA      720

GTAACATTGG AAGTAAAAGA AGGAACCGTT ACTTTAAGTA AGGAAATTGC AAAATCTGGA      780

GAAGTAACAG TTGCTCTTAA TGACACTAAC ACTACTCAGG CTACTAAAAA AACTGGCGCA      840

TGGGATTCAA AAACTTCTAC TTTAACAATT AGTGTTAACA GCAAAAAAAC TACACAACTT      900

GTGTTTACTA ACAAGACAC AATAACTGTA CAAAAATACG ACTCCGCAGG TACCAATTTA      960

GAAGGCACAG CAGTCGAAAT TAAAACACTT GATGAACTTA AAAACGCTTT AAAATAA       1017
```

(2) INFORMATION FOR SEQ ID NO:10:

(i) SEQUENCE CHARACTERISTICS:
        (A) LENGTH: 338 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: BORELLIA BURGDORFERI
        (B) STRAIN: ACAI (vii) IMMEDIATE SOURCE:
        (B) CLONE: NS1-ACA1

(xi) SEQUENCE DESCRIPTION: SEQ ID NO:10:

```
Met Asp Pro Asn Thr Val Ser Ser Phe Gln Val Asp Ser Phe Leu Trp
1               5                   10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Gly Lys Gln Asn Val Ser Ser Leu Asp Glu Lys Asn Ser Ala Ser
                85                  90                  95

Val Asp Leu Pro Gly Glu Met Lys Val Leu Val Ser Lys Glu Lys Asp
            100                 105                 110

Lys Asp Gly Lys Tyr Ser Leu Lys Ala Thr Val Asp Lys Ile Glu Leu
        115                 120                 125

Lys Gly Thr Ser Asp Lys Asp Asn Gly Ser Gly Val Leu Glu Gly Thr
    130                 135                 140

Lys Asp Asp Lys Ser Lys Ala Lys Leu Thr Ile Ala Asp Asp Leu Ser
145                 150                 155                 160

Lys Thr Thr Phe Glu Leu Phe Lys Glu Asp Gly Lys Thr Leu Val Ser
                165                 170                 175
```

```
Arg Lys Val Ser Ser Lys Asp Lys Thr Ser Thr Asp Glu Met Phe Asn
            180                 185                 190

Glu Lys Gly Glu Leu Ser Ala Lys Thr Met Thr Arg Glu Asn Gly Thr
            195                 200                 205

Lys Leu Glu Tyr Thr Glu Met Lys Ser Asp Gly Thr Gly Lys Ala Lys
            210                 215                 220

Glu Val Leu Lys Asn Phe Thr Leu Glu Gly Lys Val Ala Asn Asp Lys
225                 230                 235                 240

Val Thr Leu Glu Val Lys Glu Gly Thr Val Thr Leu Ser Lys Glu Ile
            245                 250                 255

Ala Lys Ser Gly Glu Val Thr Val Ala Leu Asn Asp Thr Asn Thr Thr
            260                 265                 270

Gln Ala Thr Lys Lys Thr Gly Ala Trp Asp Ser Lys Thr Ser Thr Leu
            275                 280                 285

Thr Ile Ser Val Asn Ser Lys Lys Thr Thr Gln Leu Val Phe Thr Lys
            290                 295                 300

Gln Asp Thr Ile Thr Val Gln Lys Tyr Asp Ser Ala Gly Thr Asn Leu
305                 310                 315                 320

Glu Gly Thr Ala Val Glu Ile Lys Thr Leu Asp Glu Leu Lys Asn Ala
            325                 330                 335

Leu Lys (2) INFORMATION FOR SEQ ID NO:11:

(i) SEQUENCE CHARACTERISTICS:
        (A) LENGTH: 1017 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: BORRELIA BURGDORFERI
        (B) STRAIN: ZS7

(vii) IMMEDIATE SOURCE:
        (B) CLONE: NS1-ZS7

(xi) SEQUENCE DESCRIPTION: SEQ ID NO:11:

ATGGATCCAA ACACTGTGTC AAGCTTTCAG GTAGATTCCT TTCTTTGGCA TGTCCGCAAA    60

CGAGTTGCAG ACCAAGAACT AGGTGATGCC CCATTCCTTG ATCGGCTTCG CCGAGATCAG   120

AAATCCCTAA GAGGAAGGGG CAGCACTCTT GGTCTGGACA TCGAGACAGC CACACGTGCT   180

GGAAAGCAGA TAGTGGAGCG GATTCTGAAA GAAGAATCCG ATGAGGCACT TAAAATGACC   240

ATGGGAAAGC AAAATGTTAG CAGCCTTGAC GAGAAAAACA GCGTTTCAGT AGATTTGCCT   300

GGTGAAATGA ACGTTCTTGT AAGCAAAGAA AAAAACAAAG ACGGCAAGTA CGATCTAATT   360

GCAACAGTAG ACAAGCTTGA GCTTAAAGGA ACTTCTGATA AAAACAATGG ATCTGGAGTA   420

CTTGAAGGCG TAAAAGCTGA CAAAAGTAAA GTAAAATTAA CAATTTCTGA CGATCTAGGT   480

CAAACCACAC TTGAAGTTTT CAAAGAAGAT GGCAAAACAC TAGTATCAAA AAAAGTAACT   540

TCCAAAGACA AGTCATCAAC AGAAGAAAAA TTCAATGAAA AAGGTGAAGT ATCTGAAAAA   600

ATAATAACAA GAGCAGACGG AACCAGACTT GAATACACAG AAATTAAAAG CGATGGATCT   660

GGAAAAGCTA AAGAGGTTTT AAAAAGCTAT GTTCTTGAAG AACTTTAAC TGCTGAAAAA   720

ACAACATTGG TGGTTAAAGA AGGAACTGTT ACTTTAAGCA AAAATATTTC AAAATCTGGG   780
```

```
GAAGTTTCAG TTGAACTTAA TGACACTGAC AGTAGTGCTG CTACTAAAAA AACTGCAGCT      840

TGGAATTCAG GCACTTCAAC TTTAACAATT ACTGTAAACA GTAAAAAAAC TAAAGACCTT      900

GTGTTTACAA AAGAAAACAC AATTACAGTA CAACAATACG ACTCAAATGG CACCAAATTA      960

GAGGGGTCAG CAGTTGAAAT TACAAAACTT GATGAAATTA AAAACGCTTT AAAATAA       1017
```

(2) INFORMATION FOR SEQ ID NO:12:

(i) SEQUENCE CHARACTERISTICS:
        (A) LENGTH: 338 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: BORRELIA BURGDORFERI
        (B) STRAIN: ZS7

(vii) IMMEDIATE SOURCE:
        (B) CLONE: NS1-ZS7

(xi) SEQUENCE DESCRIPTION: SEQ ID NO:12:

```
Met Asp Pro Asn Thr Val Ser Ser Phe Gln Val Asp Ser Phe Leu Trp
 1               5                  10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
    50                  55                  60

Val Glu Arg Ile Leu Lys Glu Ser Asp Glu Ala Leu Lys Met Thr
65                  70                  75                  80

Met Gly Lys Gln Asn Val Ser Ser Leu Asp Glu Lys Asn Ser Val Ser
                85                  90                  95

Val Asp Leu Pro Gly Glu Met Asn Val Leu Val Ser Lys Glu Lys Asn
            100                 105                 110

Lys Asp Gly Lys Tyr Asp Leu Ile Ala Thr Val Asp Lys Leu Glu Leu
        115                 120                 125

Lys Gly Thr Ser Asp Lys Asn Asn Gly Ser Gly Val Leu Glu Gly Val
    130                 135                 140

Lys Ala Asp Lys Ser Lys Val Lys Leu Thr Ile Ser Asp Asp Leu Gly
145                 150                 155                 160

Gln Thr Thr Leu Glu Val Phe Lys Glu Asp Gly Lys Thr Leu Val Ser
                165                 170                 175

Lys Lys Val Thr Ser Lys Asp Lys Ser Ser Thr Glu Glu Lys Phe Asn
            180                 185                 190

Glu Lys Gly Glu Val Ser Glu Lys Ile Ile Thr Arg Ala Asp Gly Thr
        195                 200                 205

Arg Leu Glu Tyr Thr Glu Ile Lys Ser Asp Gly Ser Gly Lys Ala Lys
    210                 215                 220

Glu Val Leu Lys Ser Tyr Val Leu Glu Gly Thr Leu Thr Ala Glu Lys
225                 230                 235                 240

Thr Thr Leu Val Val Lys Glu Gly Thr Val Thr Leu Ser Lys Asn Ile
                245                 250                 255

Ser Lys Ser Gly Glu Val Ser Val Glu Leu Asn Asp Thr Asp Ser Ser
            260                 265                 270
```

-continued

```
Ala Ala Thr Lys Lys Thr Ala Ala Trp Asn Ser Gly Thr Ser Thr Leu
        275             280             285

Thr Ile Thr Val Asn Ser Lys Lys Thr Lys Asp Leu Val Phe Thr Lys
        290             295             300

Glu Asn Thr Ile Thr Val Gln Gln Tyr Asp Ser Asn Gly Thr Lys Leu
305                 310             315                 320

Glu Gly Ser Ala Val Glu Ile Thr Lys Leu Asp Glu Ile Lys Asn Ala
                325             330             335

Leu Lys
```